United States Patent [19]

Teshima et al.

[11] Patent Number: 4,960,963
[45] Date of Patent: Oct. 2, 1990

[54] PROCESS FOR PRODUCING VINYLCHLORIDE MONOMER BY PYROLYSIS OF 1,2-DICHLOROETHANE

[75] Inventors: Yutaka Teshima, Shinnanyo; Satoshi Onishi, Tokuyama, both of Japan

[73] Assignee: Tosoh Corporation, Shinnanyo, Japan

[21] Appl. No.: 463,855

[22] Filed: Jan. 12, 1990

Related U.S. Application Data

[63] Continuation of Ser. No. 125,136, Nov. 25, 1987, abandoned.

[30] Foreign Application Priority Data

Nov. 29, 1986 [JP] Japan .................................. 61-283083

[51] Int. Cl.$^5$ ............................................. C07L 17/34
[52] U.S. Cl. .................................................. 570/226
[58] Field of Search .......................................... 570/226

[56] References Cited

FOREIGN PATENT DOCUMENTS 1127669 7/1982 Canada ................................. 570/226

Primary Examiner—Howard T. Mars
Attorney, Agent, or Firm—Oblon, Spivak, McClelland, Maier & Neustadt

[57] ABSTRACT

Process for producing vinylchloride monomer by pyrolysis of 1,2-dichloroethane comprising carrying out heat exchange between a high temperature cracked gas produced as a result of the pyrolysis product and the 1,2-dichloroethane which is introduced into the pyrolysis furnace with a flow rate of the cracked gas at 5 m/s or more but less than 20 m/s until the cracked gas is cooled down to 180°–350° C. and introducing the 1,2-dichloroethane into the furnace for the pyrolysis.

8 Claims, 1 Drawing Sheet

PROCESS FOR PRODUCING VINYLCHLORIDE MONOMER BY PYROLYSIS OF 1,2-DICHLOROETHANE

This application is a continuation of Ser. No. 07/125,136, filed on Nov. 25, 1987, now abandoned.

BACKGROUND OF THE INVENTION

1. Field of the Invention:

The present invention relates to a process for producing vinylchloride monomer (hereinafter designated as VCM) by the pyrolysis of 1,2-dichloroethane (hereinafter designated as EDC) under pressure.

2. Discussion of Background:

Prior art methods for the production of VCM teach that purified EDC in a liquid form is introduced in a preheated zone of the pyrolysis furnace under a pressure and, after being evaporated in an evaporation zone, is thermally decomposed at a temperature range from 480 to 550° C. in a pyrolysis reaction zone, to produce VCM.

In this treatment the cracked gas at a high temperature which flows out of the pyrolysis furnace mostly contains VCM and hydrogen chloride produced by the pyrolysis and the EDC remaining undecomposed. Usually the abundant heat of the cracked gas at a high temperature is exhausted away from the system with cooling water in a quencher which follows in the operation line. In the next step of operation, hydrogen chloride and the EDC remaining undecomposed are separated from VCM by use of a distillation column.

When the high temperature furnace for pyrolysis of EDC is operated for a long period of time, rigid coke is generally formed on the inside of the pyrolysis tube line. Therefore it is necessary to stop the operation before the pressure loss of the pyrolysis furnace itself exceeds the tolerance limit and decoke.

The rate of pyrolysis of EDC, or the yield of VCM per unit amount of EDC introduced in the pyrolysis furnace, can be enhanced by elevating the temperature at which the pyrolysis reaction takes place. As a result of the treatment, however, by-products such as methylchloride and butadiene which may cause trouble by polymerization are also increased. These by-products require a large amount of energy to be removed in the following stage.

Further, in the pyrolysis furnace where EDC is preheated, evaporated and decomposed by heat, the elevated temperature inside the furnace promotes the formation of rigid coke on the inside wall of the tubes, which consequently shortens the life of the pyrolysis furnace.

In addition, the elevated temperature at which the exhaust gas after combustion is exhausted from the pyrolysis furnace brings about a large increase in the loss of thermal energy.

For these reasons, temperature of the pyrolysis reaction of EDC in the actual operations is limited by the amounts of by-products and the coke which may be formed. In other words, the rate of pyrolysis can not reasonably be increased beyond a certain level.

For reducing the amount of coking formed in the tubes of the pyrolysis furnace, Japanese Laid-Open patent application No. Sho 49-125306 proposes a process in which EDC is evaporated on the outside of the pyrolysis furnace or, in other words, gaseous EDC is introduced into the pyrolysis furnace.

This process, however, requires a high temperature heat source for the evaporation of EDC and therefore a heating furnace for EDC is needed in addition to the pyrolysis furnace.

Further, additional problems of the heating furnace itself are deterioration of EDC due to the high temperature and necessity for removing scales. Thus, the expense for the operation and equipment result in an increase in the cost.

On the other hand, the cracked gas flowing out of the pyrolysis furnace contains a tremendous amount of heat energy, so that tremendous heat energy is lost to the cooling water in a quencher located immediately after the pyrolysis furnace.

A variety of methods have been proposed for recovering and utilizing the energy of the high temperature cracked gas flowing out of the pyrolysis furnace.

For instance, Japanese Laid-Open patent application No. Sho 56-45424 describes a method in which a cracked gas flowing out of a pyrolysis furnace is cooled in at least two steps and the heat transferred to a heat transfer medium is used to heat other devices.

The heat transfer medium should be selected based on consideration of resistance against the high temperature deterioration and the specific properties of the gas flowing out of the pyrolysis furnace. Precautions must be taken to avoid explosion on leakage due to hydrogen chloride or other compounds contained in the gas.

In particular, when water or stream is used as heat transfer medium, leakage of hydrogen chloride may cause severe corrosion and even breakage of equipment. In this case, the apparatus should be reconstructed on a larger scale, to utilize the recovered heat.

Japanese Laid-Open patent application No. Sho 55-129233 discloses a process in which the heat of cracked gas is indirectly exchanged using a heat transfer medium and the heat transfer medium is employed as a heat source for a distillation column for EDC, as an example of using the heat transfer medium for a heat source in another operation.

Here, troublesome operations are usually required, for example, because the distillation column is under the influence of the variations in the operating conditions of the pyrolysis furnace. Furthermore, since a pyrolysis furnace usually is situated some distance apart from a distillation column, this operation necessarily requires a large expense for equipment.

Another process is also proposed in which the exchange of heat between a cracked gas flowing from a pyrolysis furnace and EDC supplied to the pyrolysis furnace is utilized to preheat or evaporate the EDC.

In this case, however, the cracked gas flows out at a relatively high rate and therefore a fairly large length is necessary for the heat transmission tube of the heat exchanger. Consequently a pressure drop in the tubes results with the heat exchanger which is located immediately after the pyrolysis furnace and this shortens the time for a continuous operation of the pyrolysis furnace. Thus, to overcome the difficulties, a large scale remodeling of the pyrolysis furnace is necessary, for example, to expand the diameter or shorten the length of the heat transmission tubes.

In order to raise the rate of pyrolysis without elevating the temperature of the pyrolysis reaction, or in other words without increasing the amount of by-products formed in the pyrolysis furnace and a loss in thermal energy, it is necessary to increase the area of reaction zone in the pyrolysis furnace without making any drastic remodeling of the furnace. Also for the reduction of coking in tubes of the pyrolysis furnace, gaseous EDC should be introduced in the pyrolysis furnace at a site which lies in a range of zones called (for liquid EDC) from the preheating zone to the evaporation zone, preferably at the entrance of the preheating zone.

The cracked gas flowing out of the pyrolysis furnace contains large amounts of thermal energy which can be recovered by exchanging heat between the cracked gas and supplied EDC and be utilized for preheating and evaporating the EDC.

However, the heat exchange operation requires an effective heat exchanger which is installed immediately after the pyrolysis furnace and performs the exchange of heat between the cracked gas and supplied EDC with an operational condition set so as to minimize the pressure drop.

For prolonged operation, it is necessary to prevent the continuous operation of the pyrolysis furnace from being interrupted by lowered capacity of the heat exchanger, increased pressure drop, and blocking of the heat exchanger due to scaling.

SUMMARY OF THE INVENTION

The present inventors have investigated how to minimize the pressure drop in the heat exchanger in which EDC introduced in the pyrolysis furnace is preheated and evaporated by the heat exchanged from the cracked gas at a high temperature and to reduce the amount of coke formed and attached onto the heat exchanger while the device is operated. They have discovered that good results are obtained when the exchange of heat between the high temperature cracked gas obtained from the pyrolysis in the furnace and the EDC to be introduced in the pyrolysis furnace is carried out until the cracked gas is cooled down to 180-350° C. and with the flow rate of the cracked gas being equal to or more than 5 m/s but less than 20 m/s, followed by introduction of the EDC in the pyrolysis furnace to perform the pyrolysis.

BRIEF DESCRIPTION OF THE DRAWINGS

A more complete appreciation of the invention and many of the intended advantages thereof will be readily obtained as the same has become better understood by reference to the following detailed description when considered in connection with the accompanying drawings, wherein.

DETAILED DESCRIPTION OF THE PREFERRED EMBODIMENTS

Figure 1:
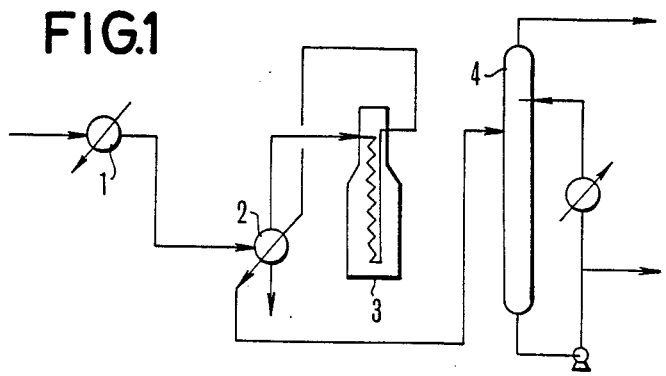
FIGS. 1 and 2 are flow sheets of the apparatus according to the process of the present invention.

The exchange of heat between a high temperature cracked gas from the pyrolysis furnace and EDC to be introduced in the pyrolysis furnace may be performed by any process, but preferably the heat exchanger is so designed that the gas is forced to flow in a heat transmitting tube and the tube is immersed in the incoming liquid EDC.

The procedure mentioned above is preferably conducted with a flow rate of cracked gas ranging from 5 m/s to less than 20 m/s.

When the flow rate of the cracked gas is less than 5 m/s, scaling comprising mainly carbon, is accelerated on the inside wall of the tube, which adversely affects the heat exchanger and in the worst case, the device may become inoperable on account of blockage of the tube.

When the flow rate of the cracked gas is 20 m/s or higher, a pressure drop in the tube, which is caused by the high rate of flow, becomes significant and must be taken into consideration.

As long as the above conditions are satisfied, any type of a heat exchanger may be employed, but preferably the heat exchanger is of a so-called mono-tube type.

The cracked gas should be preferably cooled down to 180-350° C. If the gas is cooled to a temperature below 180° C., unwanted condensation and a lowered rate of flow of the gas may occur at the lower temperatures, which may eventually completely block the tube. On the other hand, if the gas is not cooled to below 350° C., insufficient heat is recovered from the high temperature cracked gas and therefore additional heat must be supplied for evaporation of EDC by means of steam or another source of heating. This is an economical disadvantage.

Liquid EDC to be supplied to the heat exchanger and to be eventually decomposed should be at a temperature between 160° C. and 250° C. EDC at a temperature below 160° C. is undesirable because the cracked gas may be cooled down to below 180° C. and this is to be avoided as mentioned above.

The exchange of heat which performs cooling of the cracked gas and preheating and evaporation of EDC to be supplied to the pyrolysis furnace can be carried out with a single heat exchanger. However, as long as the above conditions are met, the same object can be attained with a plurality of separate heat exchange devices. For example, one may be a heat exchanger which mostly preheats the EDC and the others may be two or more heat exchangers which mostly contribute to evaporation of the EDC.

The gaseous EDC flowing out of the heat exchanger does not contain much mist or tiny drops of liquid ED and is substantially gaseous EDC. It is introduced in the pyrolysis furnace at the site which ranges from the preheating to the evaporating zone, preferably at the preheating zone, for liquid EDC.

In this manner, the gaseous EDC can be introduced into the pyrolysis furnace without making any change or with only a slight change to a conventional pyrolysis furnace, to permit the reaction zone to be enlarged in the pyrolysis furnace.

The enlarged zone described above for the pyrolysis reaction enables the rate of pyrolysis of EDC or, in other words, the amount of VCM produced per unit amount of EDC supplied to be increased by approximately 5-10% without any increase in the amount of unwanted by-products, any elevation of temperature after combustion of an exhaust gas from the pyrolysis furnace, and any consequent increase of loss in thermal energy.

Further, the amount of coke produced concurrent with a pressure drop, in the pyrolysis furnace is also decreased by 70-90%, compared with the case when EDC in the liquid form was introduced in the pyrolysis furnace.

It was amazing to find that, after a long time of operation of the heat exchanger to evaporate liquid EDC, the decrease in the purity of the EDC remaining in the heat exchanger was negligibly small and the gaseous EDC introduced in the pyrolysis furnace was as pure as the liquid EDC supplied to the heat exchanger.

This fact is markedly observed when a part, or more particularly 5-10%, of the liquid EDC supplied to the heat exchanger is extracted from the bottom of the heat exchanger and 95-90% is evaporated and introduced in the pyrolysis furnace.

Even after a long time of operation, no decrease in the purity was observed with the EDC remaining in the heat exchanger and the gaseous EDC to be introduced in the pyrolysis furnace.

In the heat exchanger in which exchange of heat was being carried out between EDC to be supplied to the pyrolysis furnace and the high temperature cracked gas flowing out of the pyrolysis furnace, it was feared that at the part of the device where EDC was being evaporated, coking would cause a decrease in the heat transmission and further disturb the operation. But surprisingly no bad effects were observed even when scales were formed. The scales were readily peeled off so as not to disturb the operation.

Other features of the invention will become apparent in the course of the following descriptions of exemplary embodiments which are given for illustration of the invention and are not intended to be limiting thereof.

EXAMPLES

In this specification, pressures are expressed by the pressure on the gauge and percentages (%) for proportions are by weight, if not otherwise specified.

EXAMPLE 1

Employing the apparatus shown in FIG. 1, a single heat exchanger 2 served to cool a high temperature cracked gas from pyrolysis furnace 3 and to preheat and evaporate EDC to be introduce in the pyrolysis furnace 3.

In this treatment, 8,600 kg/hr of liquid EDC under a pressure of 36 atm was preheated up to 190° C. in heat exchanger 1 and supplied to the bottom of heat exchanger 2.

Cracked gas flowing out of pyrolysis furnace 3 (8,600 kg/hr, 500° C. and 23 atm) was delivered at a flow rate of 9.2-13.8 m/s into the tube-side of the heat exchanger 2, to exchange heat with the fresh EDC.

Through the procedure above, the cracked gas leaving heat exchanger 2 was at 245° C. and further cooled to 80° C. in quencher 4 before being lead to next step of operation.

The total amount of the EDC supplied was evaporated and turned into a vapor at 265° C., which was then delivered to pyrolysis furnace 3 at the part previously called the preheating zone, so as to be decomposed thermally.

The cracked gas contained 3,200 kg/hr of VCM and also butadiene and methylchloride in amounts of 4.3 and 35 ppm by weight, respectively, per unit VCM. After a continuous operation for 95 days conducted under the above-mentioned conditions, the increase in the pressure drop of the pyrolysis furnace 4 was 1.3 times as much owing to the coking on the inside of tubes of the pyrolysis furnace 4.

Further, scales, of which carbon was the main ingredient, were formed on the outer surface of the tube in heat exchanger 2 which the liquid EDC contacted, but most of the scales were peeled off. A small amount of coking could be found attached to the inside of the tube at the inlet part. The cracked gas made contact with the whole inside wall of the tube, but the metal surface remained uncoated except at the inlet part only. The capacity of operation was lowered by not more than 10 % of the original capacity and therefore no obstacle was observed for the operation.

The expenditure of energy from heat exchanger 1 through pyrolysis furnace 3 amounted to 71% of that estimated in Comparison Example 1 of this specification.

EXAMPLE 2

Figure 2:
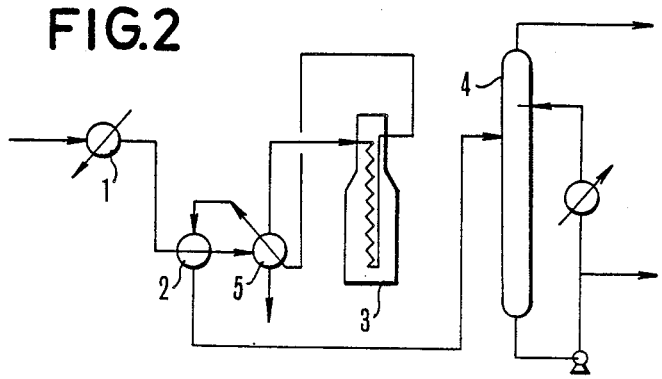

The following procedure was carried out using the apparatus shown in FIG. 2.

Liquid EDC in an amount of 8,600 kg/hr under an applied pressure 36 atm was preheated to 160° C. with steam in heat exchanger 1 and then lead to heat exchanger 2 through which flowed 8,600 kg/hr of a cracked gas at 235° C. coming from the pyrolysis furnace 3 through heat exchanger 5 for the first cooling step.

The entire amount of liquid EDC heated to 190° C. in the heat exchanger 2 was further introduced in the bottom of the heat exchanger 5.

The cracked gas, after the second cooling in the heat exchanger 2, was at a temperature of 210° C. and this was lead to a conventional quencher 4 to be cooled to 80° C.

Flow rate of the cracked gas was controlled in a range from 8.3 to 13.8 m/s in the heat exchanger.

The EDC introduced into heat exchanger 5 exchanged heat with the cracked gas (500° C. and 23 atm) and was evaporated into a vapor at 265° C. This vapor was then transferred to the pyrolysis furnace 3 at the site of preheating zone, as it is called in convention processes, to perform the pyrolysis.

In this process 3,170 kg/hr of VCM were obtained in the pyrolysis furnace 3 which contained 3.6 and 32 ppm by weight of butadiene and methylchloride, respectively, per unit VCM.

Expensive fuel supplied to the pyrolysis furnace 3 was 67% as much as that used in Comparison Example 1 of this specification. After continuous operation for about 70 days conducted under the same conditions, increase in the pressure drop in the pyrolysis furnace 3 due to the coke which deposited on the inside wall of tubes in the pyrolysis furnace 3 proved to be approximately 1.3 times as much.

Further, carbon scales formed on the outer surface of the tube in the heat exchangers 2 and 5 with which the liquid EDC contacted, but most of the scales were peeled off. A small amount of coking could be found attached to the inside of the tube at the inlet part. The cracked gas made contact with the whole inside wall of the tube, but the metal surface remained uncoated except at the inlet part only. The capacity of operation was lowered by not more than 10% of the original one capacity and therefore no obstacle was observed for the operation.

After a 70 day operation, the liquid EDC remaining in the heat exchanger 5, which was concerned mainly with the evaporation of EDC, changed concentration by 0.5% lower than that of the originally supplied EDC, but only a negligible influence was observed on the pyrolysis reaction.

COMPARISON EXAMPLE 1

Figure 3:
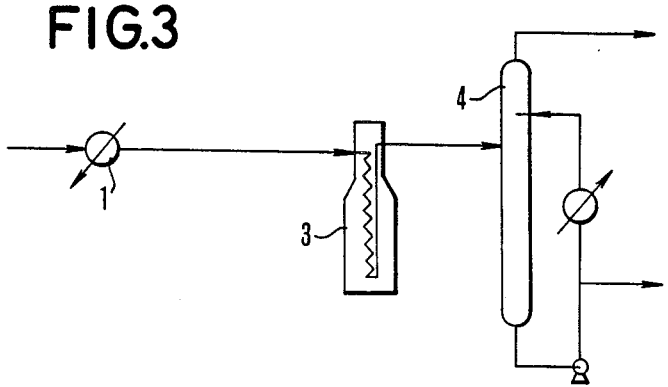
FIG. 3 is a flow sheet of an apparatus according to the process of the Comparison Example.

Decomposition of EDC was carried out using an apparatus shown in FIG. 3.

Liquid EDC (8,600 kg/hr) was preheated to 160° C. with steam in heat exchanger 1 under an applied pressure of 33 atm and delivered as it was in the liquid form to pyrolysis furnace 3 at the preheating zone for EDC.

In this manner, the liquid EDC supplied was heated to about 260° C. in the tube of the pyrolysis furnace 3 and then completely evaporated in the evaporation zone and further incompletely decomposed by heat in the pyrolysis reaction zone.

The gas produced by the pyrolysis reaction was at a temperature of 510° C. just after the pyrolysis. This was directly lead to quencher 4 and cooled there to a temperature of 80° C. before transferred to the next step of operation.

The gas produced by the pyrolysis reaction contained 2,960 kg/hr of VCM and further butadiene and methyl-chloride in amounts of 6 and 40 ppm by weight, respectively, per unit VCM.

After continuous operation for 82 days under the same conditions, rigid coke was formed and attached to the inside of the tube of pyrolysis furnace 3, which lead to about 1.5 times as much pressure drop as that at the original stage with pyrolysis furnace 3.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. A process for producing vinyl chloride monomer by the pyrolysis of 1,2-dichloroethane, comprising the steps of:
   (i) feeding liquid 1,2-dichloroethane to a heat exchange means to produce substantially gaseous 1,2-dichloroethane;
   (ii) feeding said substantially gaseous 1,2-dichloroethane into a pyrolysis furnace to produce a high temperature crack gas; and
   (iii) exchanging heat between said liquid 1,2-dichloroethane and said high temperature cracked gas in said heat exchange means; wherein said cracked gas has a flow rate of 5 m/s to less than 20 m/s and exchanging heat until said cracked gas is cooled to a temperature of 180–350° C.

2. The process of claim 1, wherein said liquid 1,2-dichloroethane is fed to said heat exchange means at a temperature between 160–250° C.

3. The process of claim 1, wherein said heat exchanging step is conducted with a single heat exchanger.

4. The process of claim 3, wherein said heat exchanger is a mono-tube heat exchanger.

5. The process of claim 1, wherein said heat exchanging step is conducted with a plurality of heat exchangers.

6. The process of claim 1, wherein said cracked gas has a flow rate of 5–13.8 m/s.

7. The process of claim 1, wherein said cracked gas has a flow rate of 8.3–13.8 m/s.

8. The process of claim 1, wherein said cracked gas has a flow rate of 9.2–13.8 m/s.

* * * * *